(12) United States Patent
Montross (10) Patent No.: US 11,413,030 B2
(45) Date of Patent: Aug. 16, 2022

(54) MONTROSS BUTTON

(71) Applicant: William Montross, Colorado Springs, CO (US)

(72) Inventor: William Montross, Colorado Springs, CO (US)

( * ) Notice: Subject to any disclaimer, the term of this patent is extended or adjusted under 35 U.S.C. 154(b) by 255 days.

(21) Appl. No.: 16/678,639

(22) Filed: Nov. 8, 2019

(65) Prior Publication Data

US 2020/0146667 A1 May 14, 2020

Related U.S. Application Data

(60) Provisional application No. 62/789,248, filed on Jan. 7, 2019, provisional application No. 62/757,631, filed on Nov. 8, 2018.

(51) Int. Cl.
*A61B 17/04* (2006.01)

(52) U.S. Cl.
CPC .. *A61B 17/0401* (2013.01); *A61B 2017/0404* (2013.01); *A61B 2017/0438* (2013.01); *A61B 2017/0464* (2013.01)

(58) Field of Classification Search
CPC .............. A61B 17/0487; A61B 17/122; A61B 2017/0404; A61B 2017/0406; A61B 2017/042; A61B 2017/0438; Y10T 24/4088; Y10T 24/4091; Y10T 24/4093
See application file for complete search history.

(56) References Cited

U.S. PATENT DOCUMENTS

| | | | | |
|---|---|---|---|---|
| 153,469 A * | 7/1874 | Wright | ................... | B65D 63/08 24/23 B |
| 168,331 A * | 10/1875 | Heaton | ..................... | A44B 1/44 24/94 |
| 177,349 A * | 5/1876 | Morehouse | .............. | A44B 1/44 24/94 |
| 193,303 A * | 7/1877 | Ward | ...................... | A41F 1/006 24/199 |
| 243,742 A * | 7/1881 | Wales | ........................ | A41F 3/00 24/315 |
| 291,275 A * | 1/1884 | Belcher, et al. | ........ | A44B 11/04 24/198 |
| 291,935 A * | 1/1884 | Prentice | ................... | A44B 1/44 24/94 |
| 298,316 A * | 5/1884 | Sanford | .................... | A44B 1/44 24/94 |
| 324,422 A * | 8/1885 | Smith Jr. | .................. | A44B 1/42 24/96 |
| 335,393 A * | 2/1886 | Steele | ...................... | A44B 1/44 24/94 |
| 336,943 A * | 3/1886 | Prentice | ................... | A44B 1/44 24/94 |
| 348,871 A * | 9/1886 | Wales | ...................... | A41F 1/006 24/199 |
| 352,039 A * | 11/1886 | Carroll | .................... | A44B 11/18 24/197 |

(Continued)

*Primary Examiner* — Tan-Uyen T Ho
*Assistant Examiner* — Charles M Wei
(74) *Attorney, Agent, or Firm* — Brainspark Associates, LLC (57) ABSTRACT

Improved methods, devices, systems and surgical techniques in the field of surgery and, in particular, improved anchoring devices and related surgical techniques for a variety of surgical repair procedures.

20 Claims, 13 Drawing Sheets

(56) References Cited

U.S. PATENT DOCUMENTS

| | | | | |
|---|---|---|---|---|
| 654,206 A | * | 7/1900 | Walker | B65D 63/08 24/23 B |
| 685,831 A | * | 11/1901 | Frawley | F16L 33/02 24/22 |
| 703,350 A | * | 6/1902 | Nonnemacher | A44B 11/04 24/198 |
| 722,375 A | * | 3/1903 | Molloy | A44B 11/04 24/198 |
| 820,710 A | * | 5/1906 | Ford | A41F 11/12 24/184 |
| 828,577 A | * | 8/1906 | Sherman | A41F 9/002 2/319 |
| 867,638 A | * | 10/1907 | Boyden | A44B 11/04 24/198 |
| 873,445 A | * | 12/1907 | Maltby | A44B 11/04 24/198 |
| 881,461 A | * | 3/1908 | Craig | A44B 11/04 24/200 |
| 912,204 A | * | 2/1909 | Tacy | A44B 11/04 24/198 |
| 1,485,266 A | * | 2/1924 | Hennah | D06F 55/00 24/570 |
| 1,545,515 A | * | 7/1925 | Phoel | A41F 5/00 24/200 |
| 1,636,925 A | * | 7/1927 | Ravigneaux | A44B 11/04 24/200 |
| 1,643,183 A | * | 9/1927 | Roland | A41F 11/16 2/318 |
| 1,768,977 A | * | 7/1930 | Ealy | A61F 13/64 24/570 |
| 1,860,170 A | * | 5/1932 | Bronson | A44B 11/04 24/198 |
| 2,095,340 A | * | 10/1937 | Meyer | A44B 11/04 24/198 |
| 2,099,199 A | * | 11/1937 | Devendor | A44B 11/04 24/198 |
| 2,140,164 A | * | 12/1938 | Moffatt | A41F 1/006 24/199 |
| 2,212,862 A | * | 8/1940 | Hirsh | A44B 11/04 24/198 |
| 2,224,773 A | * | 12/1940 | Shaulson | A44B 11/28 24/200 |
| 2,226,262 A | * | 12/1940 | Roberts | A41F 11/02 24/323 |
| 2,229,003 A | * | 1/1941 | Fly | A44B 11/065 242/388.2 |
| 2,613,420 A | * | 10/1952 | Brown | A44B 11/04 24/200 |
| 2,643,431 A | * | 6/1953 | Schwarz | A41F 15/002 24/200 |
| 3,218,686 A | * | 11/1965 | Rubenstein | A44B 11/04 24/198 |
| 3,636,597 A | * | 1/1972 | Barnickel | B65D 63/16 24/198 |
| 4,291,698 A | * | 9/1981 | Fuchs | A61B 17/0487 606/232 |
| 4,607,415 A | * | 8/1986 | Fukuroi | A44B 1/44 24/94 |
| 4,807,622 A | * | 2/1989 | Ohkaka | A61B 17/122 30/124 |
| 4,823,794 A | * | 4/1989 | Pierce | A61B 17/0401 606/232 |
| 5,084,946 A | * | 2/1992 | Lee | A44B 11/006 24/200 |
| 5,282,832 A | * | 2/1994 | Toso | A61B 17/0487 24/DIG. 50 |
| D359,229 S | * | 6/1995 | Jules | D8/395 |
| 5,432,985 A | * | 7/1995 | Bernart | A44B 11/04 24/200 |
| 5,584,105 A | * | 12/1996 | Krauss | A44B 11/263 24/614 |
| 5,584,835 A | * | 12/1996 | Greenfield | A61B 17/0401 606/232 |
| 5,662,133 A | * | 9/1997 | Guido, Jr. | E04H 15/64 135/119 |
| 5,991,986 A | * | 11/1999 | Canna | A44B 11/006 24/197 |
| 6,546,601 B1 | * | 4/2003 | Kawashima | A44B 11/04 24/200 |
| 7,299,527 B1 | * | 11/2007 | Gyure | A44B 11/006 24/198 |
| D576,867 S | * | 9/2008 | Kretz | D8/356 |
| D600,673 S | * | 9/2009 | Kim | D14/205 |
| 8,747,439 B2 | * | 6/2014 | Bonutti | B29C 66/69 606/232 |
| 9,034,001 B2 | * | 5/2015 | Cheng | A61B 17/0487 606/151 |
| 10,085,740 B1 | * | 10/2018 | Anderson | A61B 17/0401 |
| 10,299,784 B2 | * | 5/2019 | Anderson | A61B 17/0401 |
| 10,470,759 B2 | * | 11/2019 | Miraki | A61B 17/0487 |
| D891,292 S | * | 7/2020 | Cardin | D11/200 |
| 11,013,506 B2 | * | 5/2021 | Moore | A61B 17/0487 |
| 2002/0077029 A1 | * | 6/2002 | Fildan | A41F 1/006 450/86 |
| 2004/0260344 A1 | * | 12/2004 | Lyons | A61B 17/0487 606/232 |
| 2005/0033361 A1 | * | 2/2005 | Galdonik | A61B 17/12109 606/213 |
| 2005/0066484 A1 | * | 3/2005 | Hum | A44B 11/04 24/321 |
| 2007/0157438 A1 | * | 7/2007 | Judd | H02G 11/02 24/115 R |
| 2011/0224700 A1 | * | 9/2011 | Schmidt | A61B 17/122 606/151 |
| 2011/0224706 A1 | * | 9/2011 | Weitzner | A61B 17/122 606/157 |
| 2011/0245855 A1 | * | 10/2011 | Matsuoka | A61B 17/1285 606/157 |
| 2012/0059394 A1 | * | 3/2012 | Brenner | A61B 17/122 606/142 |
| 2012/0123541 A1 | * | 5/2012 | Albertorio | A61F 2/0811 623/13.14 |
| 2012/0150203 A1 | * | 6/2012 | Brady | A61B 17/0401 606/148 |
| 2013/0110164 A1 | * | 5/2013 | Milazzo | A61B 17/0487 606/232 |
| 2013/0168478 A1 | * | 7/2013 | Holman | B65H 75/446 242/118 |
| 2013/0245653 A1 | * | 9/2013 | Litherland | A61B 17/128 606/158 |
| 2013/0325063 A1 | * | 12/2013 | Norton | A61B 17/0401 606/232 |
| 2014/0031864 A1 | * | 1/2014 | Jafari | A61B 17/0487 606/232 |
| 2014/0058411 A1 | * | 2/2014 | Soutorine | A61B 17/1285 606/142 |
| 2014/0250636 A1 | * | 9/2014 | Vantrease | B65D 33/1625 24/30.5 S |
| 2018/0185154 A1 | * | 7/2018 | Cao | A61F 2/2463 |
| 2018/0255881 A1 | * | 9/2018 | Sorensen | A44B 11/065 |
| 2018/0333156 A1 | * | 11/2018 | Hayashi | A61B 17/1285 |
| 2019/0150929 A1 | * | 5/2019 | Gregan | A61B 17/1285 |
| 2019/0159783 A1 | * | 5/2019 | Lehtinen | A61B 17/122 |
| 2019/0167260 A1 | * | 6/2019 | Levinson | A61L 31/041 |
| 2019/0284014 A1 | * | 9/2019 | Pollock | B65H 75/4473 |

* cited by examiner

FIG. 25

MONTROSS BUTTON

CROSS-REFERENCE TO RELATED APPLICATIONS

This application claims the benefit of U.S. Provisional Patent Application Ser. No. 62/757,631 entitled "MONTROSS BUTTON" filed Nov. 8, 2018 and U.S. Provisional Patent Application Ser. No. 62/789,248 entitled "MONTROSS BUTTON" filed Jan. 7, 2019, the disclosures of which are each hereby incorporated by reference in their entireties.

TECHNICAL FIELD

The invention relates to the field of surgery and, in particular, relates to improved anchoring devices and related surgical techniques for a variety of surgical repair procedures and, in particular, to various suture buttons or suture anchor-button designs for use in a variety of surgical repair techniques.

BACKGROUND OF THE INVENTION

Disruption of various ligaments and/or other soft tissue structures within the human anatomy is a common occurrence. In many cases, the injury might be treated conservatively and the only residual problem is that of a mild cosmetic deformity, while in other cases the joint may be reduced acutely and held reduced during the healing phase, allowing the native ligaments to heal and restore some or all of the stability of the joint. Several groups of patients, however, do not tolerate the injury well, and/or some cases may require surgical reattachment of soft tissues where complete detachment and/or other disruption may have occurred.

In many cases, a selected surgical treatment may involve the use of surgical bolts, stables and hooks, while others may involve sutures and/or various anchoring devices. In some surgeries, sutures may be attached to an external plate or button, which may abut against a bony or other structure into which the suture extends.

There are a wide variety of existing external anchoring plates and/or surgical buttons, but these devices have various limitations.

BRIEF SUMMARY OF THE INVENTION

Various embodiments of the present invention include the realization of a need in the art for surgical anchoring devices and anchoring button designs that allow for easy placement and/or removal, thereby facilitating surgical techniques for various types of joint repair, as well as use during revision procedures.

In various embodiments, a surgical button is shown which includes a plate portion and at least one externally accessible slot having a slot opening which can accommodate a suture, tape, wire or other flexible surgical anchoring device. Desirably, the one or more slot will allow a suture or suture loop to be drawn or pulled into contact with a portion of the plate, wherein the slot and/or other plate features will retain the suture therein without requiring a surgeon to "thread" a suture end through the opening, as is done with current button anchor designs. Such an arrangement not only facilitates the speed of initially implanting the surgical button anchor, but the present design also allows for installation of anchoring components during revision surgeries, without requiring severing and/or removal of existing sutures and/or anchoring devices in certain embodiments.

In a variety of embodiments, the suture button can include an anchoring plate having a plurality of slots and a plurality of retaining tabs, which allow a suture or suture tab to be slid into the slots and retained/locked into the plate by the retaining tabs.

Another object of the invention is to allow for placement, replacement and/or removal of button anchors to sutures and/or suture tapes already secured within patient anatomy.

BRIEF DESCRIPTION OF THE SEVERAL VIEWS OF THE DRAWINGS

The foregoing and other objects, aspects, features, and advantages of embodiments will become more apparent and may be better understood by referring to the following description, taken in conjunction with the accompanying drawings, in which.

DETAILED DESCRIPTION OF THE INVENTION

As discussed herein, the present invention includes various methods, devices, systems and surgical techniques which significantly improve the anchoring of sutures and the like in patient tissues. In various embodiment, a surgical button is depicted which can include a plate portion and at least one externally accessible slot having a slot opening which accommodates a suture, tape, wire or other flexible surgical anchoring device. Desirably, the one or more slot will allow a suture or suture loop to be drawn or pulled into contact with a portion of the plate, wherein the slot and/or other plate features will retain the suture therein without requiring a surgeon to "thread" a suture end through the opening, as is done with current button anchor designs. Such an arrangement not only facilitates the speed of initially implanting the surgical button anchor, but the present design also allows for installation of anchoring components during revision surgeries, without requiring severing and/or removal of existing sutures and/or anchoring devices in certain embodiments FIGS. 1 through 5 depict various views of an anchoring button 10 constructed in accordance with various embodiments of the present invention. The anchoring button 10 includes a generally flat, planer base 20, with a central prong 30 having an arrowhead-shaped distal head 80, with flanking arms 40 and 50 extending from the base 20 on each side of the central prong 30. A pair of retaining barbs 90 and 95 are formed on a proximal portion of the distal end 80, and a pair of inwardly extending shield portions 60 and 70 extend from distal ends of the flanking arms 40. Desirably, the central prong 30 and the flanking arms 40 and 50 will form one or more slots 100 and 105 in the anchoring button 10 for accommodating one or more sutures or suture tapes (not shown), with the barbs 90, 95 and the shield portions 60, 70 cooperating to retain the suture within the slots 100, 105 in a desired manner.

While the disclosed embodiments disclose a substantially flat, planar base, it should be understood that, in other exemplary embodiments, the base may comprise a curved and/or rounded base on one or both sides that could be concave and/or convex in nature, as well as more complex shapes that could be various combinations of flat, convex, concave and/or other shapes.

Figure 1:
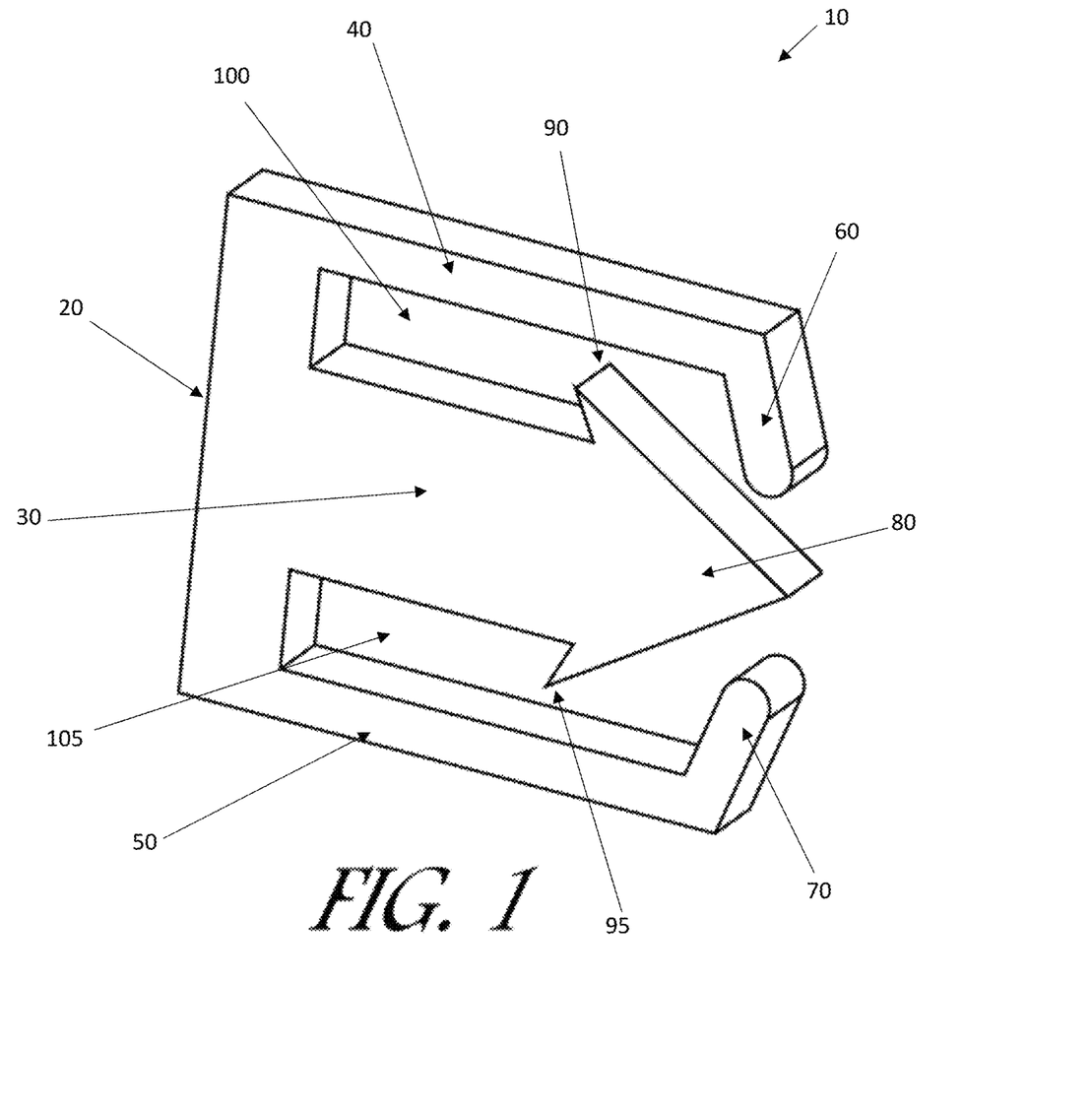
FIG. 1 depicts a perspective view of one exemplary embodiment of an anchoring button.
Figure 2:
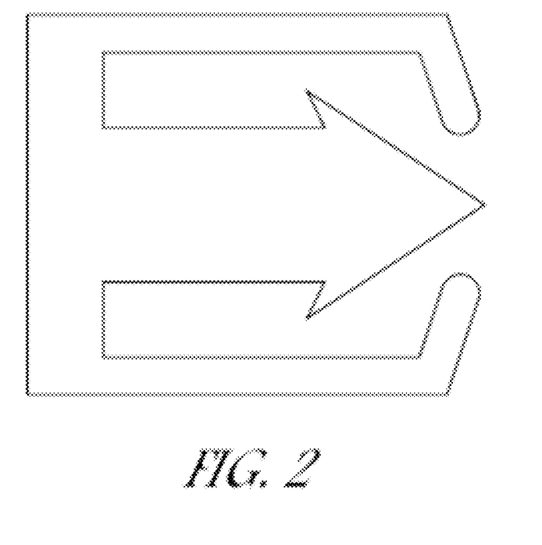
FIG. 2 depicts a front view of the anchoring button of FIG. 1.
Figure 3:
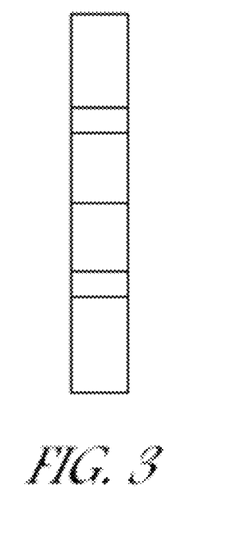
FIG. 3 depicts a side view of the anchoring button of FIG. 1.
Figure 4:
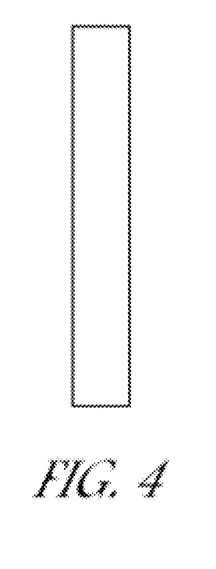
FIG. 4 depicts an opposing side view of the anchoring button of FIG. 1.
Figure 5A:
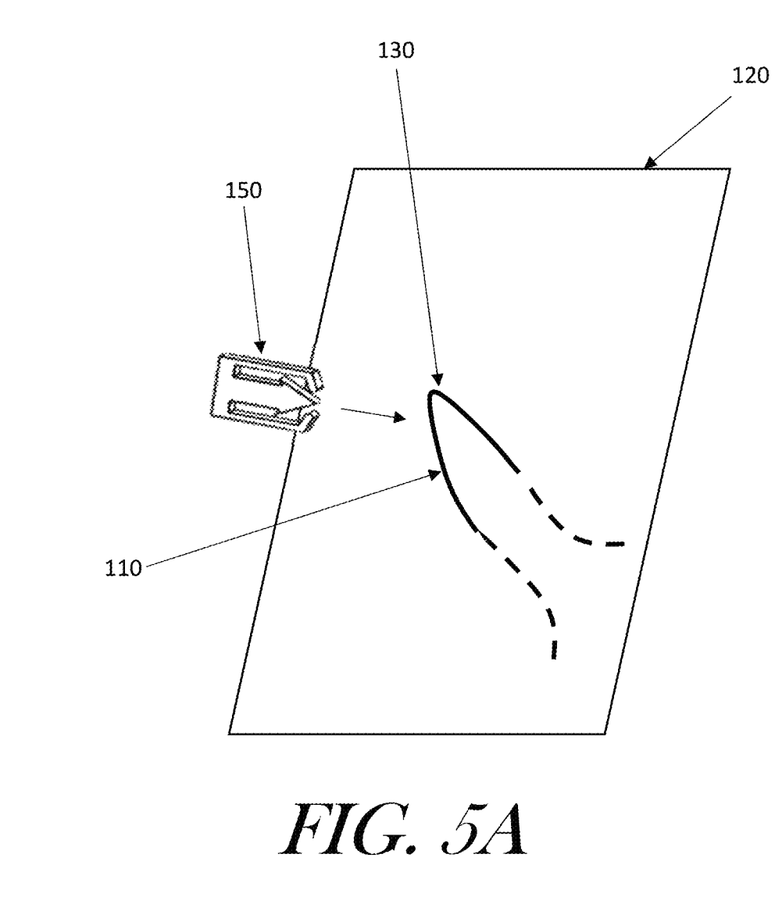
FIG. 5A depicts an exemplary approach for securing the anchoring button of FIG. 1 to a suture loop.
Figure 5B:
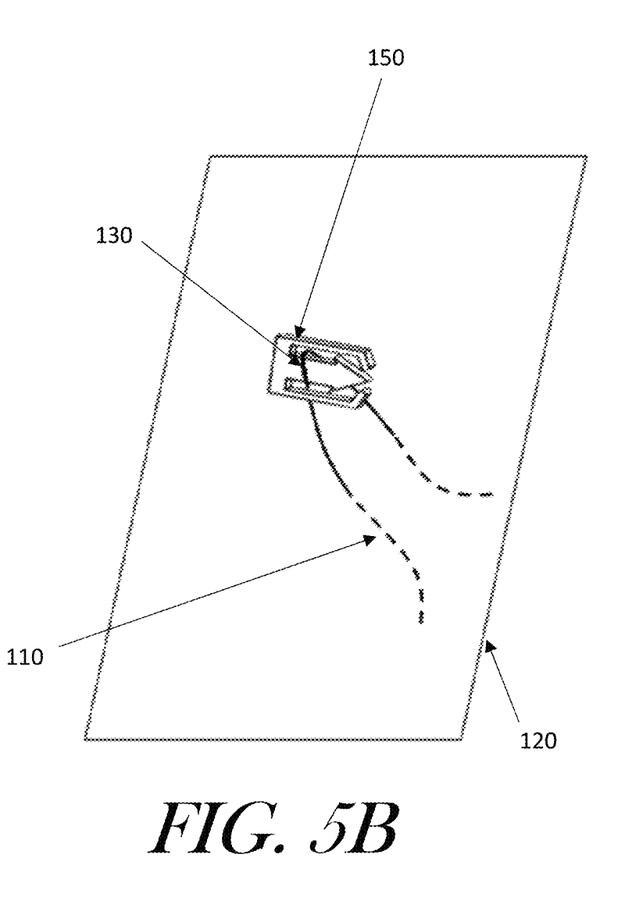
FIG. 5B depicts an exemplary placement of the anchoring button of FIG. 1 on a suture loop.

In use, as best seen in FIGS. 5A and 5B, a surgeon can place a suture 110 into and/or through a tissue layer 120, and if desired can create a suture loop 130 extending back into the tissue layer 120, and an anchoring button 150 can be advanced through suture loop 130, with the sutures 110 desirably extending through the slots of the anchoring button 150 with the suture loop 130 extending around the central prong of the anchoring button. The suture can then be tightened by the surgeon, wherein the anchoring button will be drawn into direct contact with tissue layer 120 as the suture passes through the slots, with the central portion contacting the tissue layer and being retained in that position by tension on the sutures.

In some alternative embodiments, especially where a far-side surgical incision is not desired, a button anchor such as disclosed herein may be deployed through a passage or opening in target tissues, with the button rotated or otherwise manipulated such that it presents a larger cross-sectional area than the hole through which it passed.

The various embodiments of surgical buttons disclosed herein are particularly easy to use during surgical procedures, in that the surgical button can be attached and/or detached from the anchoring suture with relative ease at virtually any time during the surgical procedure. Moreover, because the slots can be parallel in some embodiments, such a design can permit a button anchor to be removed from a patient with little or no need to loosen the underlying suture, if desired. In various embodiments, sutures such as those disclosed herein can be utilized over an existing fracture plate for syndesmotic repair or similar procedures.

The various design features of the anchoring button also significantly increase the strength and durability of the anchoring construct as compared to prior art devices. For example, the various button designs disclosed in the present invention present significant amounts of surface are to the underlying support tissue, which helps to prevent tissue damage and/or "pull through" of the anchoring button during periods of significant stresses. In addition, the arrangement of the various components of the button anchor significantly improve the button's ability to accommodate and distribute forces that it experiences, in that the flanking arms and/or base components can individually flex and/or bend relative to the central prong, which can reduce loading and/or damage to underlying tissues and well as reduce and/or prevent breakage and/or failure of the button.

In various embodiments, the anchoring button can comprise a variety of materials appropriate for use in surgical procedures, including various plastics, metals and/or ceramic materials. In some embodiments, the surgical button can comprise a plate or disc-like structure of a suitable non-metallic material, such as nylon. Desirably, the button will have at least one opening and slot extending axially into the button body, and in many embodiments will comprise a plurality of openings and/or slots extending therein. If desired, the upper and lower faces of the button can comprise a similar material and/or structure, or the opposing faces can comprise differing materials and/or features/textures.

In various embodiments, a suture button can include a plate, button or similar device that allows cordage, suture, tape and/or the like to lock into, slide into and/or slide over a portion of the of the device (or a combination of lock, slide and/or pass over the device) to secure tissue to tissue, bone to bone, and or tissue to bone. In various embodiments, the design of the device and/or tensioning of the suture will allow the suture, cordage or tape to remain in place, while in other alternative embodiments the device may incorporate a movable arm(s) or leg(s), or other wedging feature, to trap and or hold the suture, cordage or tape therein.

FIGS. 6 through 10 depict various views of an alternative embodiment of an anchoring button 200 constructed in accordance with various embodiments of the present invention. In this embodiment, the button 200 includes an elongated, generally rectangular shaped body having a centrally located stem 210 with an arrowhead-shaped distal end 220, with flanking arms 230 and 240 extending on each side of the central stem 210 to form a pair of elongated slots 250 and 255. A pair of retaining barbs 260 and 265 are formed on the central stem 210, with distal portions of the flanking arms 230 and 240 generally coterminous with the distal end 220.

Figure 6:
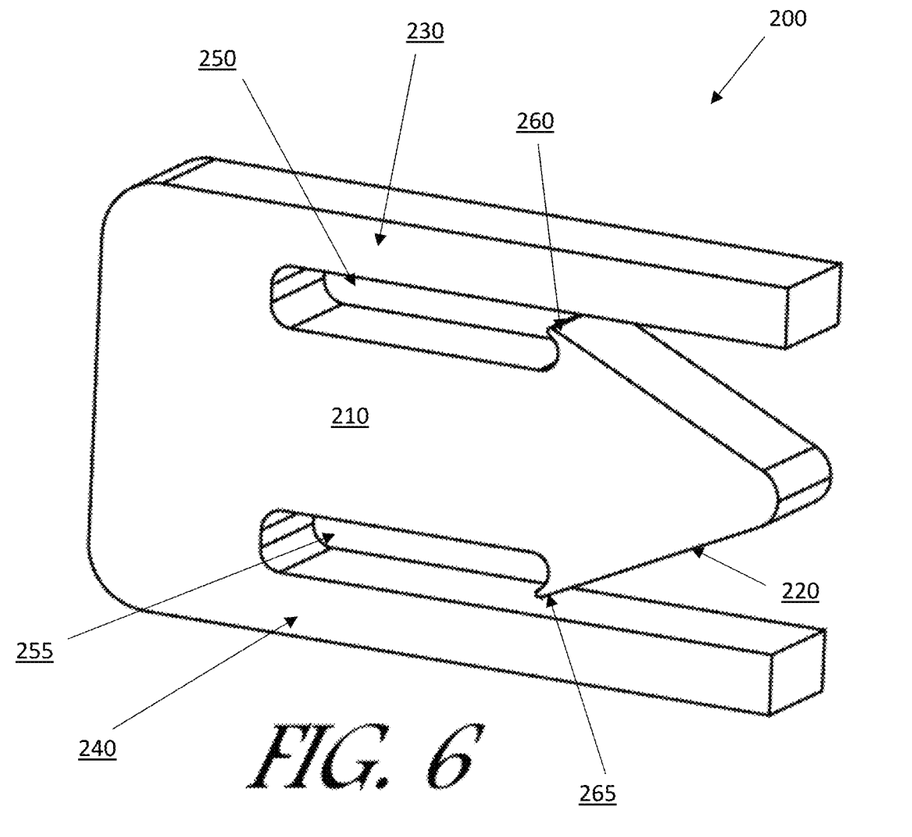
FIG. 6 depicts a perspective view of another exemplary embodiment of an anchoring button.
Figure 7:
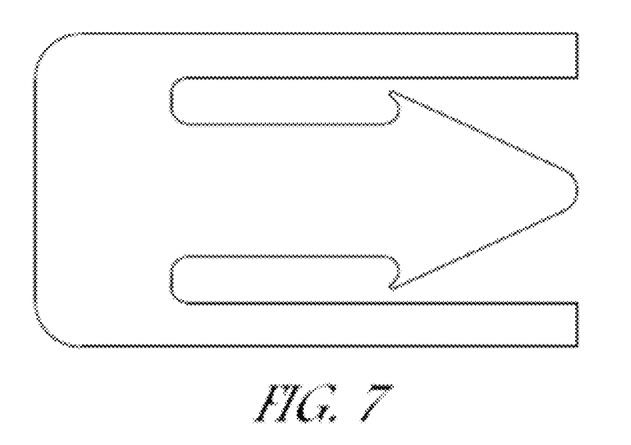
FIG. 7 depicts a front view of the anchoring button of FIG. 6.
Figure 8:
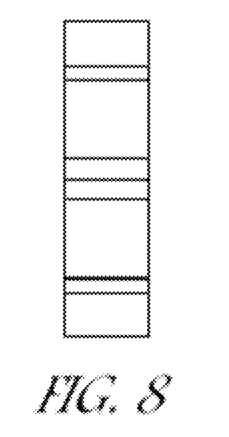
FIG. 8 depicts a side view of the anchoring button of FIG. 6.
Figure 9:
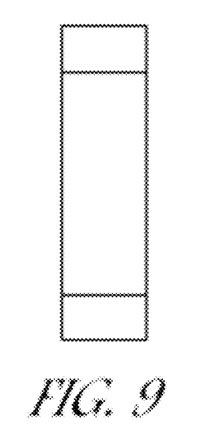
FIG. 9 depicts an opposing side view of the anchoring button of FIG. 6.
Figure 10:
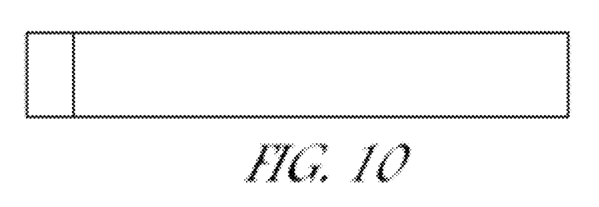
FIG. 10 depicts a top plan view of the anchoring button of FIG. 6.
Figure 11:
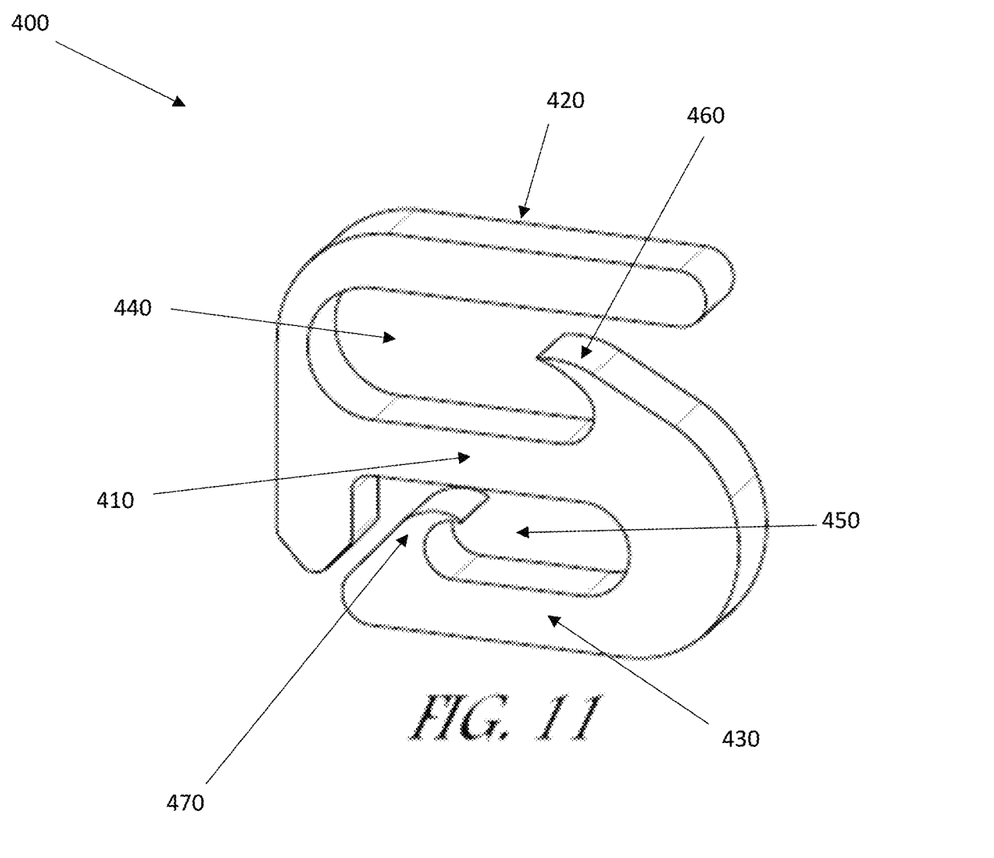
FIG. 11 depicts a perspective view of another exemplary embodiment of an anchoring button.
Figure 12:
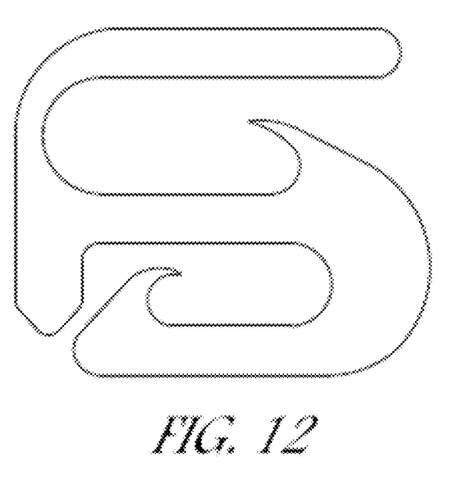
FIG. 12 depicts a front view of the anchoring button of FIG. 11.
Figure 13:
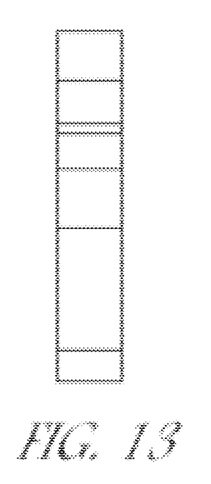
FIG. 13 depicts a side view of the anchoring button of FIG. 11.
Figure 14:
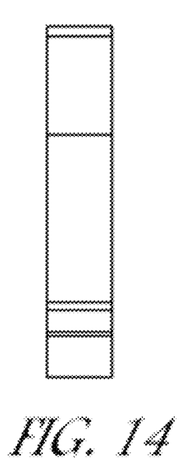
FIG. 14 depicts an opposing side view of the anchoring button of FIG. 11.
Figure 15:
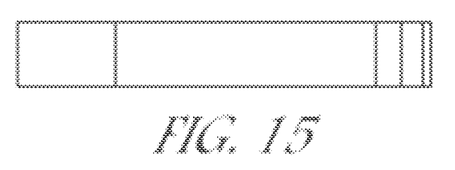
FIG. 15 depicts a top plan view of the anchoring button of FIG. 11.
Figure 16:
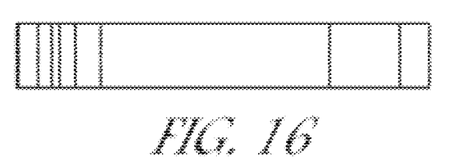
FIG. 16 depicts a bottom plan view of the anchoring button of FIG. 11.

In this embodiment, the anchoring button 200 may be sized and configured such that a space between a retaining barb 260 and an inner wall of the flanking arm 230 can be slightly less than the diameter of a suture to be placed therein (not shown), such that some degree of flexion of the barb 260 and/or arm 230 (and/some flexion of the suture) may be necessary or desirable to allow the suture to pass into the slot 250—thereby allowing the suture to be captured and/or "locked" within the slot 250 in a desired manner. In other alternative embodiments, the spacing between the barb and the arm may be greater and/or smaller, and in some embodiment the barb may be in direct contact with the arm.

In the embodiment of FIG. 6, the retaining barbs can incorporate a scalloped, undercut or curved section which faces towards the slot, which can serve to assist with suture retention within the slot.

In various alternative embodiments, the flanking arms and/or other features of the button may include plastically deformable elements, which could allow the button to be "crimped" or otherwise deformed to enclose and/or wedge a suture or tape in the button in a desired manner.

In one exemplary embodiment, an anchoring button may be constructed 7 mm across its width (i.e., from flanking arm 230 to flanking arm 240) with a height of 9.5 mm (from base to distal end 220), with a button thickness of 0.5 mm to 1 mm, a slot width of 1 mm, and a clearance width (between the barb and flanking arm) of approximately 0.3 mm.

FIGS. 11 through 16 depict various views of another alternative embodiment of an anchoring button 400 constructed in accordance with various embodiments of the present invention. In this embodiment, the button 400 includes a central stem 410 with flanking arms 420 and 430 extending from opposing sides of the stem 410. In this embodiment, the flanking arms 420 and 430 include curved portions that extend back towards the stem to form a pair of elongated slots 440 and 450. The button also includes various barbs 460 and 470 which substantially close outward portions of the slots. In this embodiment, the flanking arms and/or barbs will desirably elastically "flex" or otherwise move to allow the suture, tape or cordage to enter each slot and be secured therein.

Figure 17:
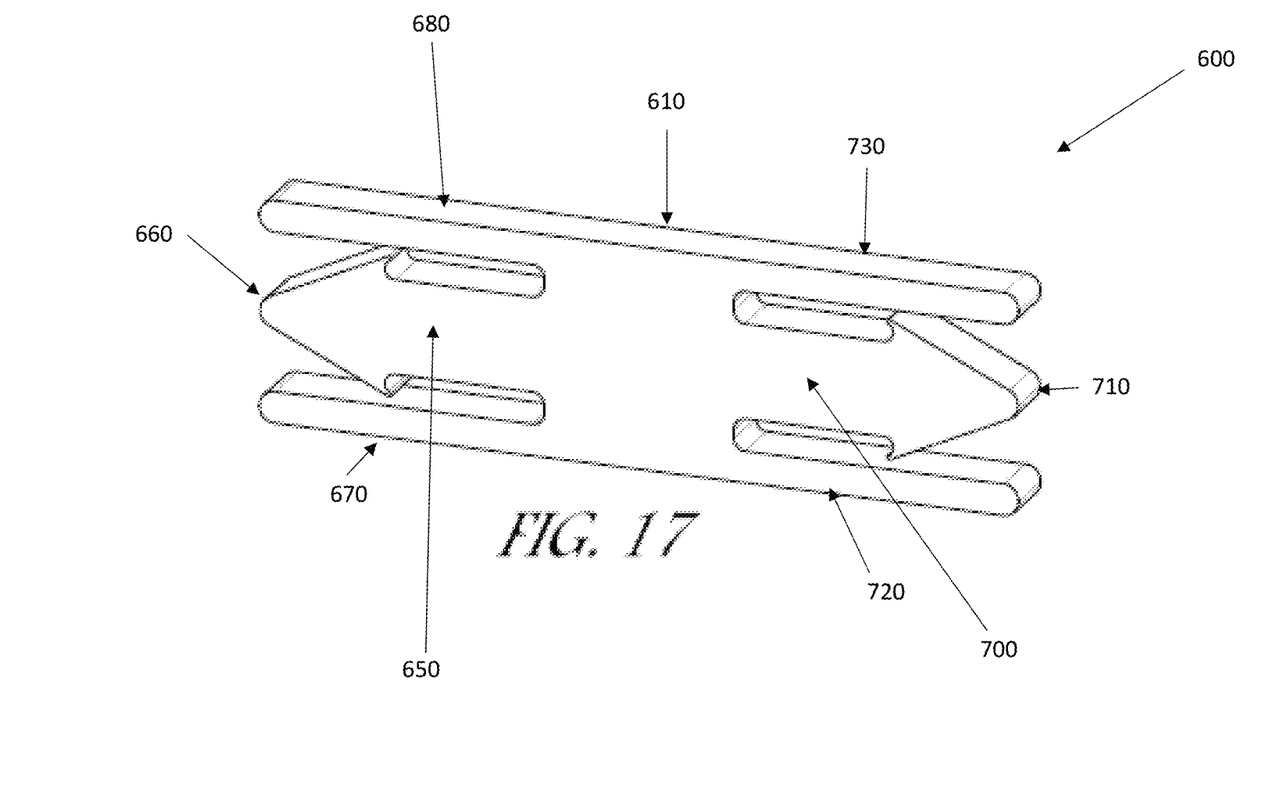
FIG. 17 depicts a perspective view of another exemplary embodiment of an anchoring button.
Figure 18A:
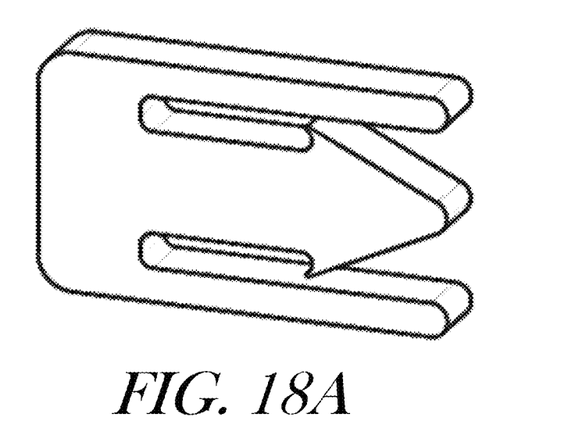
FIG. 18A depicts a perspective view of another exemplary embodiment of an anchoring button.
Figure 18B:
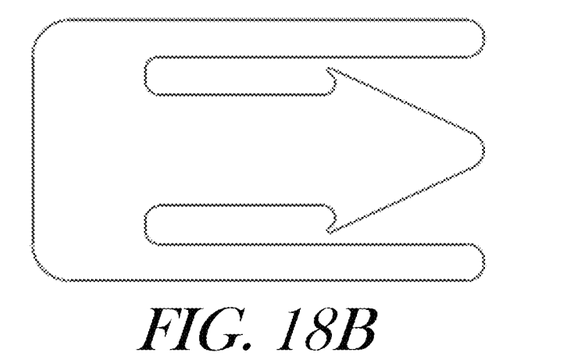
FIG. 18B depicts a front view of the anchoring button of FIG. 18A.
Figure 18C:
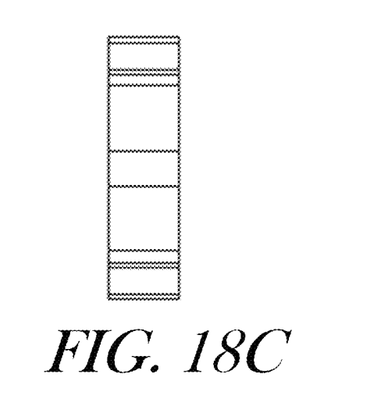
FIG. 18C depicts a side view of the anchoring button of FIG. 18A.
Figure 18D:
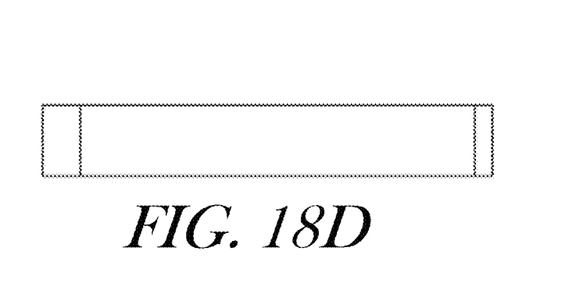
FIG. 18D depicts a bottom plan view of the anchoring button of FIG. 18A.
Figure 18E:
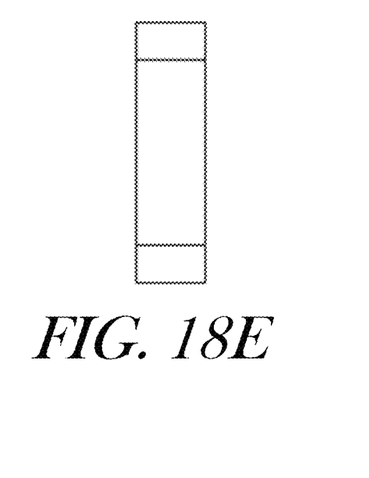
FIG. 18E depicts an opposing side view of the anchoring button of FIG. 18A.

FIG. 17 depicts a perspective view of another alternative embodiment of an anchoring button 600 constructed in accordance with various embodiments of the present invention. In this embodiment, the button 600 can include an elongated body 610 with a first central stem 650 extending outwardly in a first direction and a second central stem 700 extending outwardly in a second direction. Each of the central stems 650 and 700 can include a respective arrow-shaped distal tip 660 and 710, with the first central stem 650 including two flanking arms 670 and 680 and the second central stem 700 including two flanking arms 720 and 730. Each of the arrowhead-shaped distal ends can include respective retaining barbs to retain sutures and the like, similar to various previously described embodiments.

FIGS. 18A through 18E depict various views of another alternative embodiment of an anchoring button constructed in accordance with various embodiments of the present invention. This embodiment, which incorporates many similar features to the embodiment of FIGS. 6 through 10, further includes various rounded and/or smoothed external surfaces, which can be particularly useful to prevent tissue irritation and/or damage or injury to various tissues and/or other surgical components, including sutures, tap, cordage and/or the like.

FIGS. 19 through 23 depict various views of another alternative embodiment of an anchoring button 800 constructed in accordance with various embodiments of the present invention. This embodiment, which incorporates many similar features to the embodiment of FIGS. 1 through 4, further includes a post 810 extending outwardly from the central stem 820. In various embodiments, the post 810 may occupy some portion of a drill channel (which may also contain a suture or other anchoring component), which can significantly improvement the stability and/or fixation of the button 800, as well as facilitate a successful surgical repair procedure.

Figure 19:
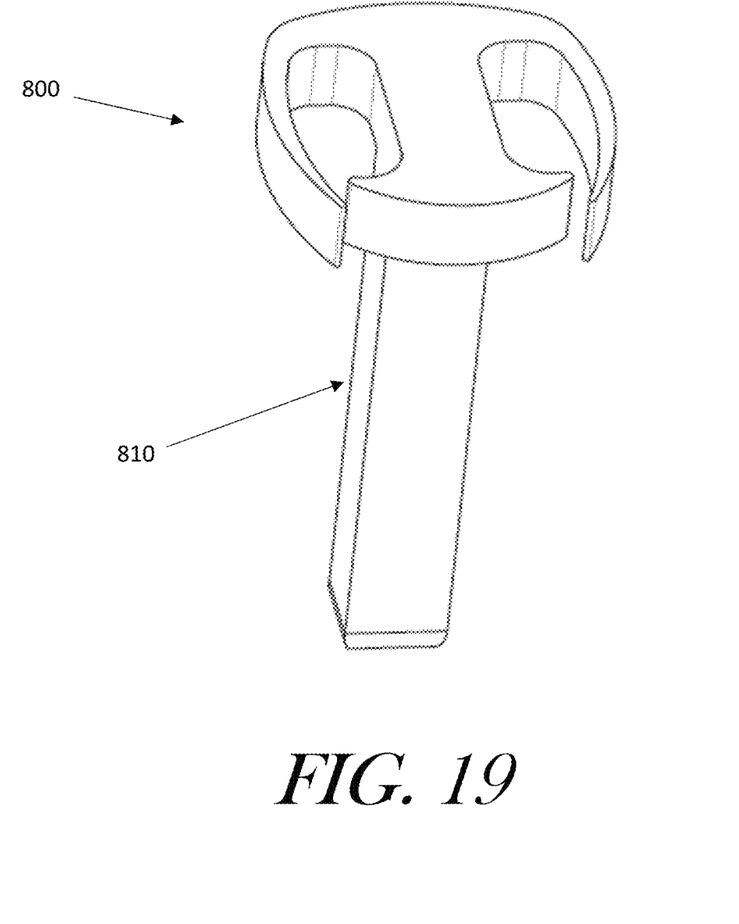
FIG. 19 depicts a perspective view of another exemplary embodiment of an anchoring button.
Figure 20:
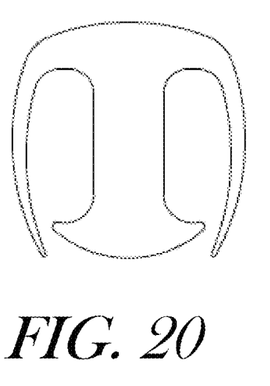
FIG. 20 depicts a top plan view of the anchoring button of FIG. 19.
Figure 21:
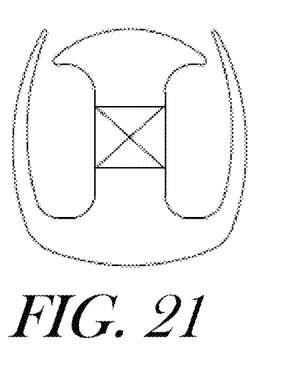
FIG. 21 depicts a bottom plan view of the anchoring button of FIG. 19.
Figure 22:
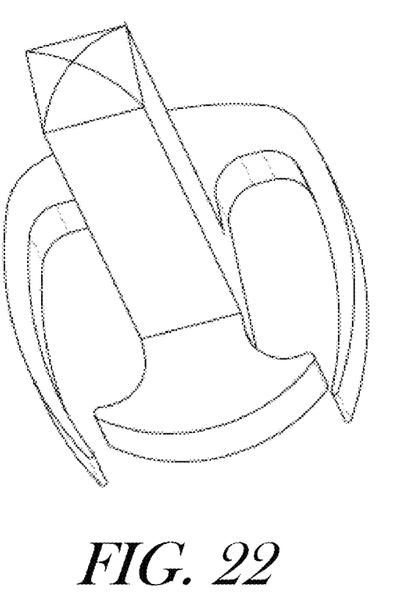
FIG. 22 depicts a lower perspective view of the anchoring button of FIG. 19.
Figure 23:
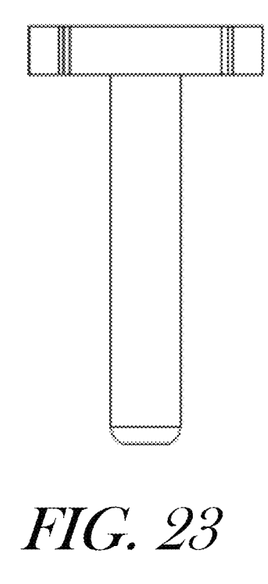
FIG. 23 depicts a side plan view of the anchoring button of FIG. 19.
Figure 24:
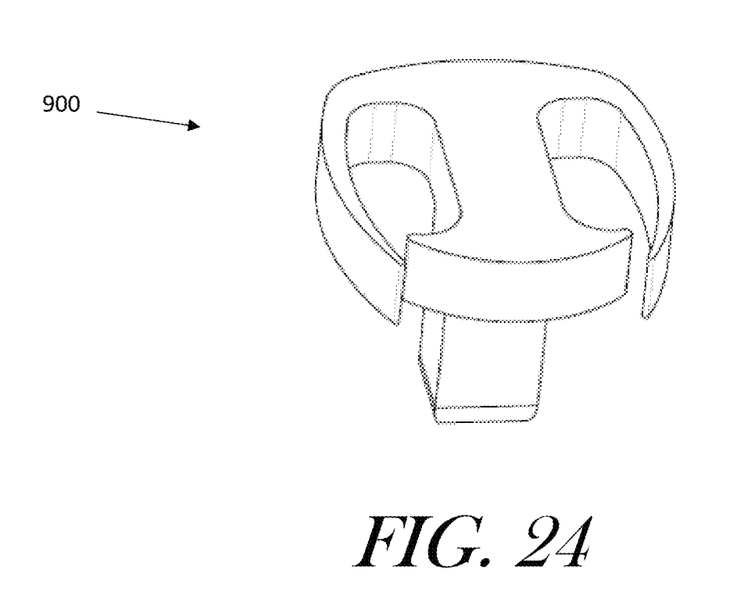
FIG. 24 depicts a perspective view of another exemplary embodiment of an anchoring button.

FIG. 24 depicts an alternative embodiment similar to the anchoring button of FIG. 19, which incorporates a shorter post. In this embodiment, the central stem may be approximately 1.5 mm in length, with a 1.5 mm post extending from the central stem. If desired, an anchoring button embodiment may be approximately 4 mm in width and height, and 4 mm depth (including the post).

Figure 25:
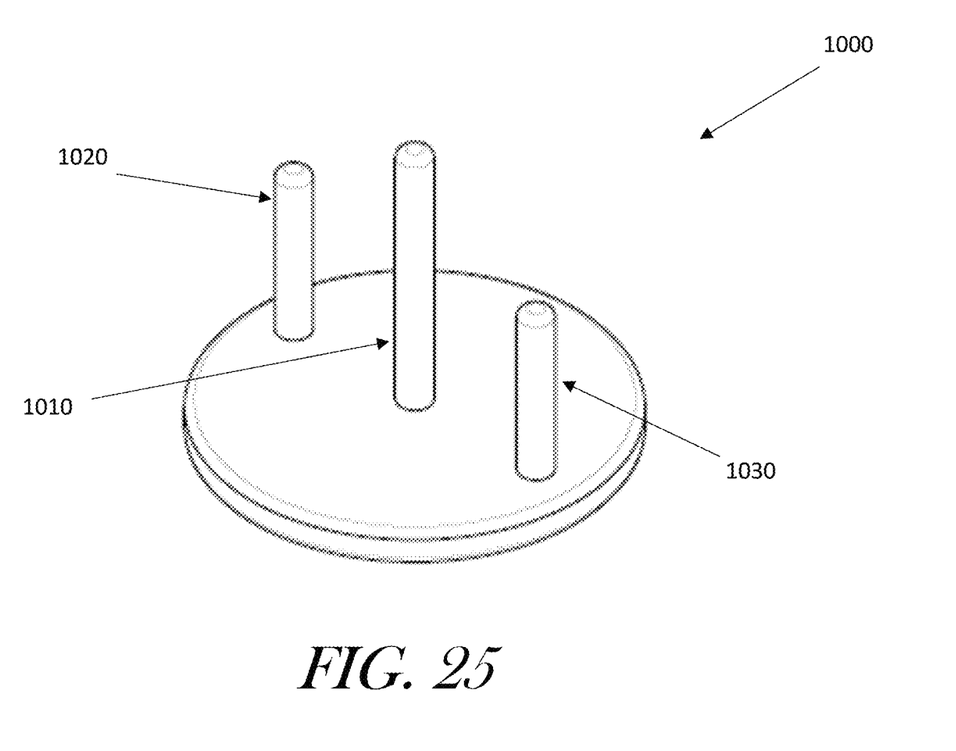
FIG. 25 depicts a perspective view of an anchoring device for a button.

FIG. 25 depicts one exemplary embodiment of a fixation device for optional use with the various button and/or other devices disclosed herein. In this embodiment are shown a plurality of fixation posts 1010, 1020 and 1030, which may be formed on an underside surface of an anchoring device 1000, such as a button anchor, and these posts may be used to stabilize and/or supplement fixation and/or placement of the button onto and/or into targeted anatomy. If desired, one, two or more fixation posts may be incorporated into an anchoring button, including the various anchoring button embodiments described herein. As shown, the fixation posts can extend perpendicularly outward (or even generally perpendicularly outward) from a surface of the anchoring device, although in alternative embodiments the fixation posts could extend at other angles from the anchoring device, including approximately 45 degrees, 60 degrees, 75 degrees, 80 degrees, 85 degrees, 89 degrees and/or various combinations thereof, including the incorporation of fixation posts of different lengths and/or directions extending from a single anchoring button.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

What is claimed is:

1. An anchor device for repairing soft tissue with a suture, comprising:
   an anchor body comprising a generally U-shaped wall having a base and pair of opposed arms, the wall having an opening formed between the pair of opposed arms;
   a prong member positioned at least partially within the opening, the prong member including a proximal portion formed integrally with the base of the generally U-shaped wall and a distal portion extending into the opening, the distal portion including a peripheral edge extending into the opening, the peripheral edge spaced apart from an inner edge of at least one of the pair of opposed arms by a minimum distance; and
   an undercut retention tab formed on the distal portion, the undercut retention tab extending from the peripheral edge towards the inner edge of the at least one of the pair of opposed arms, with an undercut section facing towards the base;
   the suture having a minimum cross-sectional width, the minimum cross-sectional width of the suture being greater than the minimum distance, whereby the at least one of the pair of opposed arms must flex relative to the prong member to thereby allow a loop of the suture to travel between the inner edge and the peripheral edge of the at least one of the pair of opposed arms.

2. The anchor device of claim 1, wherein the generally U-shaped wall of the anchor body is substantially flat.

3. The anchor device of claim 1, wherein the generally U-shaped wall of the anchor body comprises a convex surface on at least one side.

4. The anchor device of claim 1, wherein at least one of the pair of opposed walls have a concave surface on at least one side.

5. The anchor device of claim 1, wherein the prong member is substantially parallel to at least one of the pair of opposed walls.

6. The anchor device of claim 1, wherein the prong member is fully within the opening.

7. The anchor device of claim 1, wherein each of the pair of opposed arms include a bent distal end the prong member.

8. The anchor device of claim 7, wherein the bent distal ends of the pair of opposed arms are bent towards each other.

9. The anchor device of claim 1, wherein, after passage of the suture, the at least one of the pair of opposed arms flexes towards the prong member to lock the suture between the inner edge and the peripheral edge.

10. The anchor device of claim 1, wherein the prong member includes a post extending outward from the prong member in a perpendicular direction.

11. An anchor device for repairing soft tissue with a suture, comprising:
   an anchor body comprising a generally U-shaped wall having a base and pair of opposed arms, the wall having an opening formed between the pair of opposed arms;
   a prong member positioned at least partially within the opening, the prong member including a proximal portion formed integrally with the base of the generally U-shaped wall and a distal portion extending into the opening, the distal portion including a peripheral edge extending into the opening, the peripheral edge spaced apart from an inner edge of at least one of the pair of opposed arms by a minimum distance; and
   an undercut retention tab formed on the distal portion, at least a portion of the undercut retention tab being flexible, the undercut retention tab extending from the peripheral edge towards the inner edge of the at least one of the pair of opposed arms, with an undercut section facing towards the base;
   the suture having a minimum cross-sectional width, the minimum cross-sectional width of the suture being greater than the minimum distance, whereby at least a portion of the undercut retention tab must flex relative to the prong member to thereby allow a loop of the suture to travel between the inner edge and the peripheral edge of the at least one of the pair of opposed arms.

12. The anchor device of claim 11, wherein the generally U-shaped wall of the anchor body is substantially flat.

13. The anchor device of claim 11, wherein the generally U-shaped wall of the anchor body comprises a convex surface on at least one side.

14. The anchor device of claim 11, wherein at least one of the pair of opposed walls have a concave surface on at least one side.

15. The anchor device of claim 11, wherein the prong member is substantially parallel to at least one of the pair of opposed walls.

16. The anchor device of claim 11, wherein the prong member is fully within the opening.

17. The anchor device of claim 11, wherein each of the pair of opposed arms include a bent distal end the prong member.

18. The anchor device of claim 17, wherein the bent distal ends of the pair of opposed arms are bent towards each other.

19. The anchor device of claim 11, wherein, after the suture travels between the inner edge and the peripheral edge, the flexible portion of the undercut retention tab flexes towards the inner edge to lock the suture between the inner edge and the peripheral edge.

20. The anchor device of claim 11, wherein the prong member includes a post extending outward from the prong member in a perpendicular direction.

* * * * *